United States Patent
Sams-Dodd et al.

(10) Patent No.: US 6,297,262 B1
(45) Date of Patent: Oct. 2, 2001

(54) TREATMENT OF SCHIZOPHRENIA AND PSYCHOSIS

(75) Inventors: Frank Sams-Dodd, Barcelona (ES); Jorn Arnt, Solrod Strand (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/424,822

(22) PCT Filed: May 28, 1998

(86) PCT No.: PCT/DK98/00220

§ 371 Date: Jan. 14, 2000

§ 102(e) Date: Jan. 14, 2000

(87) PCT Pub. No.: WO98/53820

PCT Pub. Date: Dec. 3, 1998

(30) Foreign Application Priority Data

May 29, 1997 (DK) .................................................. 0620/97

(51) Int. Cl.[7] ............................................................ A61K 31/44
(52) U.S. Cl. ..................................................................... 514/340
(58) Field of Search ................................................. 514/340

(56) References Cited

U.S. PATENT DOCUMENTS

| | | | |
|---|---|---|---|
| 4,112,101 | 9/1978 | Sellstedt et al. | 514/340 |
| 4,769,379 | 9/1988 | Lietold et al. | 514/290 |
| 4,837,241 | 6/1989 | Jensen et al. | 514/340 |
| 4,933,353 | 6/1990 | Jensen et al. | 514/340 |
| 4,968,691 | 11/1990 | Orlek et al. | 514/305 |
| 5,041,455 | 8/1991 | Sauerberg et al. | 514/342 |
| 5,073,560 | 12/1991 | Wu et al. | 514/278 |
| 5,242,927 | 9/1993 | Baker et al. | 514/299 |
| 5,328,925 | 7/1994 | Sauerberg et al. | 514/342 |
| 5,405,853 | 4/1995 | Baker et al. | 514/299 |
| 5,523,314 | 6/1996 | Bue-Valleskey et al. | 514/369 |
| 5,585,388 | 12/1996 | Cosford et al. | 514/343 |
| 5,686,473 | 11/1997 | Cosford et al. | 514/357 |
| 5,691,365 | 11/1997 | Crooks et al. | 514/343 |
| 5,705,512 | 1/1998 | Mc Donald et al. | 514/343 |
| 5,736,560 | 4/1998 | Cosford et al. | 514/343 |
| 5,739,119 | 4/1998 | Galli et al. | 514/44 |
| 5,741,802 | 4/1998 | Kem et al. | 514/334 |
| 5,756,501 | 5/1998 | Sabb | 514/248 |

FOREIGN PATENT DOCUMENTS

| | | | |
|---|---|---|---|
| 0 296 721 A2 | 5/1988 | (EP) | C07D/211/04 |
| 296 721 | 12/1988 | (EP) | C07D/211/04 |
| 0 525 879 A1 | 7/1992 | (EP) | C07D/401/04 |
| WO 93/19062 | 3/1993 | (WO) | C07D/413/04 |
| 95/05174 | 2/1995 | (WO) | A61K/31/44 |

OTHER PUBLICATIONS

CA127:9136, Pike, 'Treatment of traumatic brain injury,' WO 9717074 A1, May 1997.*
Appel, S.H., "Current Neurolgy" vol. 6, p. 313–317.
Birdsall, N.J.M., et al., Proc.R.Soc. Lond.B, 207, 1–12, 1980.
Flood, J., et al,"Memory retention test performance in Mice: improvement by chronic oral cholinergic drug treatment" CA 101:83883, 1984.
Freedman, E.A. et al., Br. J. Pharmacol., 93:437–445, 1988.
Larsson, C., et al. "In vitro binding of 3H–acetylcholine to Nicotininc Receptors in Rodent and Human Brain" CA 107:71323, 1987.
Marx, J., "Human Brain Disease Recreated in Mice", Science, vol. 250, p 1509–1510, 1990.
Moltzen, E.K., et al., J. Med. Chem., 37:4085–4099, 1994.
Stevenson T., "Drug Therapy in the Management of Parkinson's Disease" Medline 09080873, 1997.

* cited by examiner

*Primary Examiner*—Rebecca Cook
(74) *Attorney, Agent, or Firm*—Darby & Darby

(57) ABSTRACT

The compound 5-(2-ethyl-2H-tetrazol-5-yl)-1,2,3,6-tetrahydro-1-methylpyridine has shown effects on models of psychosis, schizophrenia and schizophreniform diseases and is useful for the manufacture of a pharmaceutical preparation for the treatment of such diseases.

6 Claims, No Drawings

TREATMENT OF SCHIZOPHRENIA AND PSYCHOSIS

This is a 371 of PCT/DK98/00220 filed May 28, 1998.

FIELD OF INVENTION

The present invention relates to the use of 5-(2-ethyl-2H-tetrazol-5-yl)-1,2,3,6-tetrahydro-1-methylpyridine for the treatment of psychosis.

BACKGROUND OF THE INVENTION

EP-A1 0 296 721 disclosed a class of piperidine or 1,2,3,6-terahydropyridine compounds substituted in the 5-position with a five-membered heterocyclic group, including a subclass of optionally substituted 5-tetrazolyl-1,2,3,6-tetrahydro-pyridine compounds. The compounds were disclosed to have high affinity to central cholinergic receptors, in particular high affinity for central muscarinic $M_1$ receptors, thus being useful in the treatment of Alzheimer's disease, senile dementia, and impaired learning and memory functions.

The structure-activity relationship of this subclass was described by Moltzen et al., *J. Med. Chem.* 1994, 37, 4085–4099. One of the compounds, i.e. 5-(2-ethyl-2H-tetrazol-5-yl)-1,2,3,6-tetrahydro-1-methylpyridine has been reported to be selective for muscarinic receptors with a several fold higher affinity for $M_1$ than for $M_2$ and $M_3$ receptors (*Subtypes of Muscarinic Receptors, The Sixth International Symposium*, Nov. 9–12, 1994, Fort Lauderdale). Functionally, it has been described to behave as a partial agonist at $M_1$ receptors and an antagonist at $M_2$ and $M_3$ receptors. Furthermore, the only prominent in vivo effect reported was effect on spatial memory acquisition in young and aged rats, respectively. Recently, the compound was disclosed to show relieving effects after traumatic brain injury, WO 97/17074.

A class of compounds previously reported to show muscarinic effects were described to be useful in the treatment of schizophrenia, cf. WO 9505174 A1 and WO 95/05379.

It has now, surprisingly, been found that the compound 5-(2-ethyl-2H-tetrazol-5-yl)1,2,3,6-tetrahydro-1-methylpyridine shows beneficial effects in the treatment of psychosis, schizophrenia, and schizophreniform diseases.

SUMMARY OF THE INVENTION

Accordingly, the present invention relates to the use of 5-(2-ethyl-2H-tetrazol-5-yl)-1,2,3,6-tetrahydro-1-methylpyridine or an acid addition salt thereof

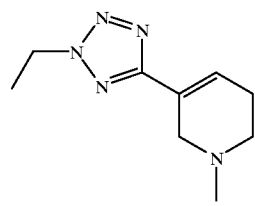

for the manufacture of a pharmaceutical preparation for the treatment of psychosis, schizophrenia, and schizophreniform diseases.

The term psychosis is in this specification meant to include all forms of psychoses, such as organic psychoses, drug induced psychoses, Alzheimer related psychoses, and psychosis or related conditions associated with other mental disorders, such as paranoid personality disorder, etc.

The terms schizophrenia and schizophreniform diseases include all types of such disorders, e.g. catatonic, disorganised, paranoid, undifferential and residual schizophrenia, and all conditions associated with such diseases, including positive and negative symptoms thereof.

The pharmaceutically acceptable acid addition salts of the compounds used in the invention are salts formed with non-toxic organic or inorganic acids. Exemplary of such organic salts are those with maleic, fumaric, benzoic, ascorbic, pamoic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic, and theophylline acetic acids, as well as the 8-halotheophyllines, for example 8-bromo-theophylline. Exemplary of such inorganic salts are those with hydrochloric, hydrobromic, sulfuric, sulfamic, phosphoric, and nitric acids.

The compound used according to the invention has now been found to be useful in the treatment of psychosis, schizophrenia, and schizophreniform diseases. So, it inhibits the effects of phencyclidine (PCP) on social interaction and PCP-induced stereotyped behaviour in rats. The effects of PCP on social interaction and other behavioural features and an animal model based thereon has been described by F. Sams-Dodd in *Behavioural Pharmacology,* 1996, 7, 3–23. The study of F. Sams-Dodd suggests that PCP-induced stereotyped behaviour and social isolation, respectively, in rats correspond to positive and negative symptoms of schizophrenia, and that PCP-treated rats respond to drug treatment in a manner that correlates well with findings in schizophrenic patients. Thus this model may determine effects of drugs on positive and negative symptoms of schizophrenia, onset of action, and side effect profile.

In another aspect, the present invention provides a method for treatment of psychosis, schizophrenia, and schizophreniform diseases in humans, comprising the step of administering a therapeutically effective amount of 5-(2-ethyl-2H-tetrazol-5-yl)-1,2,3,6-tetrahydro-1-methylpyridine or an acid addition salt thereof to a patient in need thereof.

The compound used according to the invention and the pharmaceutically acceptable acid addition salts thereof may be administered in any suitable way, e.g. orally or parenterally, and the compounds may be presented in any suitable form for such administration, e.g. in the form of tablets, capsules, powders, syrups, or solutions or dispersions for injection.

An effective daily dose of the compound according to the invention or a pharmaceutically acceptable salt thereof is from 10 μg/kg to 10 mg/kg body weight, preferably 25 mg/day/kg body weight to 1.0 mg/day/kg body weight. Accordingly, a suitable daily dose is 500 μg to 600 mg/day, preferably 1.0 mg to 100 mg.

The compound used according to the invention may be obtained as described in EP-A1 0 296 721 and the acid addition salts thereof are easily prepared by methods well known in the art.

Pharmacology

The compound used according to the invention was tested by the method described by F. Sams-Dodd, 1996, supra:

Phencyclidine-induced stereotyped behaviour and social isolation in rats. Young male Witar rats (Charles River, Germany) weighing 320–420 g were used. The rats were kept in a reversed light cycle (light 18.00 h–06.00 h). Further details regarding the design of the model appears from F. Sams-Dodd, 1996, supra: and F. Sams-Dodd, *J. Neurosci. Methods.* 59, 1995, 157–168.

The test was performed in an open arena (L, W, H: 150×100×40 cm) with bottom and sides covered with a black non-reflecting material. The behaviour of the rats were recorded by a video camera.

The rats were placed in the experimental room one day before testing. During the test period the rats received daily injections s.c. with test compound and PCP (7.1 μmol/kg) for three days. 30 mins after the last injection and in the period from 08.00 h to 14.00 h the rats were subjected to the test. Two rats, one white and one coloured black, having received identical treatment and being unfamiliar to each other, were placed in the unfamiliar test arena. The rats were videofilmed for 10 mins and returned to their cages. Rats receiving test compound and vehicle were used as control groups.

The social interaction between the rats were analysed as described in the above references. The following parameters were determined:

Travelled Distance: Total travelled distance during the observation period. This is a measure of locomotor activity.

Percent time in central zone: The arena was divided in a central and a peripheral zone that covered 33% and 66% of the arena, respectively.

Social Interaction: Duration of social behaviour between the rats during the observation period measured as the number of observations in which the centres of gravity of the rats were closer than 20 cm apart. This number was divided by the sampling rate to express the parameter in seconds.

Active social interaction: Duration of social behaviour while the rat was actively moving around.

Passive social interaction: Duration of social behaviour while the rat was inactive.

Stereotyped behaviour and ataxia were rated off-line by trained observers. Each videorecording was viewed for 60 s halfway through the 10 min. observation period, and each rat was scored after the scales of Castellani and Adams Eur. J. Pharmacol., 73, 1981, 143–154, as described in F. Sams-Dodd, 1996, supra.

Results

The compound of the invention was found to improve active social interaction in PCP-treated rats in doses of 5 μmol/kg or larger. Furthermore, it inhibits PCP-induced stereotyped behaviour in rats.

FORMULATION EXAMPLES

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, lactose, talcum, magnesium stearate, gelatine, lactose, gums, and the like. Any other adjuvant or additive colourings, aroma, preservatives etc. may be used provided that they are compatible with the active ingredients. Solutions for injections may be prepared by solving the active ingredient and possible additives in a part of the vehicle, preferably sterile water, adjusting the solution to the desired volume, sterilization of the solution, and filling in suitable ampules or vials. Any suitable additive conventionally used in the art may be added, such as tonicity agents, preservatives, antioxidants, etc.

Typical examples of recipes for the formulations of the invention are as follows (amounts of active ingredient calculated as the free base):

| 1) | Tablets: | |
|---|---|---|
| | Comp. of invention | 20 mg |
| | Lactose | 60 mg |
| | Maize starch | 30 mg |
| | Hydroxypropylcellulose | 2.4 mg |
| | Microcrystalline cellulose | 19.2 mg |
| | Croscarmellose Sodium Type A | 2.4 mg |
| | Magnesium stearate | 0.84 mg |
| 2) | Tablets: | |
| | Comp. of invention | 10 mg |
| | Lactose | 46.9 mg |
| | Maize starch | 23.5 mg |
| | Povidone | 1.8 mg |
| | Microcrystalline cellulose | 14.4 mg |
| | Croscarmellose Sodium Type A | 1.8 mg |
| | Magnesium stearate | 0.63 mg |
| 3) | Syrup: | |
| | Comp. of invention | 5.0 mg |
| | Sorbitol | 500 mg |
| | Hydroxypropylcellulose | 15 mg |
| | Glycerol | 50 mg |
| | Methyl-paraben | 1 mg |
| | Propyl-paraben | 0.1 mg |
| | Ethanol | 0.005 ml |
| | Flavour | 0.05 mg |
| | Saccharin sodium | 0.5 mg |
| | Water | ad 1 ml |
| 4) | Solution: | |
| | Comp. of invention | 1.0 mg |
| | Sorbitol | 5.1 mg |
| | Acetic acid | 0.08 mg |
| | Water for injection | ad 1 ml |

What is claimed is:

1. A method of treating psychosis, schizophrenia and schizophreniform diseases, comprising administering a therapeutically effective amount of 5-(2-ethyl-2H-tetrazol-5-yl)- 1,2,3,6-tetrahydro-1-methylpyridine (Formula (I))

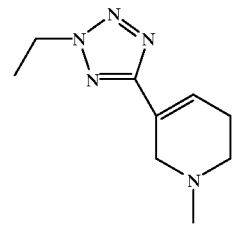

or a pharmaceutically acceptable acid addition salt thereof, to a person in need of said treatment.

2. The method of claim 1, wherein 5-(2-ethyl-2H-tetrazol-5-yl)-1,2,3,6-tetrahydro-1-methylpyridine or a pharmaceutically acceptable acid addition salt thereof is in unit dosage form.

3. The method of claim 2, wherein 5-(2-ethyl-2H-tetrazol-5-yl)-1,2,3,6-tetrahydro-1-methylpyridine or a pharmaceutically acceptable acid addition salt thereof is present in an amount of 500 μg to 600 mg per day.

4. The method of claim 2, wherein 5-(2-ethyl-2H-tetrazol-5-yl)-1,2,3,6-tetrahydro-1-methylpyridine or a pharmaceutically acceptable acid addition salt thereof is present in an amount of 1.0 mg to 100 mg per day.

5. The method of claim 1, for treating positive and negative symptoms of schizophrenia.

6. The method of claim 5, for treating positive symptoms of schizophrenia.

* * * * *